(12) United States Patent
Phillips et al.

(10) Patent No.: US 8,773,239 B2
(45) Date of Patent: Jul. 8, 2014

(54) BIOMETRIC IDENTIFICATION SYSTEM USING PULSE WAVEFORM

(75) Inventors: Brian K. Phillips, Lakewood, CO (US); Geoffrey A. Wilson, Roseburg, OR (US)

(73) Assignee: Integrated Monitoring Systems, LLC, Lakewood, CO (US)

(*) Notice: Subject to any disclaimer, the term of this patent is extended or adjusted under 35 U.S.C. 154(b) by 87 days.

(21) Appl. No.: 13/079,219

(22) Filed: Apr. 4, 2011

(65) Prior Publication Data
US 2012/0253154 A1 Oct. 4, 2012

(51) Int. Cl.
| A61B 5/1455 | (2006.01) |
| A61B 5/02 | (2006.01) |
| A61B 5/0402 | (2006.01) |
| A61B 5/026 | (2006.01) |

(52) U.S. Cl.
USPC .......................................... 340/5.82; 600/301

(58) Field of Classification Search
CPC ........ A61B 5/021; A61B 5/026; A61B 5/117; A61B 5/14551; A61B 8/06; G05B 1/00
USPC ........................... 340/5.82; 600/301; 180/272
See application file for complete search history.

(56) References Cited

U.S. PATENT DOCUMENTS

| 5,220,919 | A | 6/1993 | Phillips et al. |
| 5,719,950 | A | 2/1998 | Osten et al. |
| 6,483,929 | B1 | 11/2002 | Murakami et al. |
| 6,985,070 | B1 | 1/2006 | Parker |
| 6,993,378 | B2 | 1/2006 | Wiederhold et al. |
| 7,002,477 | B1 | 2/2006 | Camhi |
| 7,388,493 | B2 | 6/2008 | Lerch et al. |
| 7,441,123 | B2 | 10/2008 | Grant et al. |
| 7,536,557 | B2 | 5/2009 | Murakami et al. |
| 7,603,887 | B2 | 10/2009 | Schlichte |
| 7,611,461 | B2 | 11/2009 | Hawthorne et al. |
| 7,616,123 | B2 | 11/2009 | Ridder et al. |
| 7,641,611 | B2 | 1/2010 | Hawthorne et al. |
| 7,756,558 | B2 | 7/2010 | Ridder et al. |
| 7,796,013 | B2 | 9/2010 | Murakami et al. |
| 2003/0135097 | A1* | 7/2003 | Wiederhold et al. .......... 600/301 |
| 2004/0236199 | A1 | 11/2004 | Hawthorne et al. |
| 2004/0239510 | A1 | 12/2004 | Karsten |
| 2007/0177770 | A1 | 8/2007 | Derchak et al. |
| 2010/0108425 | A1* | 5/2010 | Crespo et al. ................. 180/272 |

FOREIGN PATENT DOCUMENTS

WO 94/07407 4/1994

OTHER PUBLICATIONS

PCT International Search Report and Written Opinion for International Application No. PCT/US2012/032014, dated Jul. 27, 2012, 10 pages.

* cited by examiner

*Primary Examiner* — Brian Zimmerman
*Assistant Examiner* — Bhavin M Patel
(74) *Attorney, Agent, or Firm* — Dorr, Carson & Birney, P.C.

(57) ABSTRACT

A method and system for biometric identity confirmation is based on the pulse wave of a subject. During an initial enrollment mode, pulse wave data for a known subject are used to generate subject characterization data for the known subject. During a subsequent operational mode, pulse wave data for a test subject are analyzed using the subject characterization data to confirm whether the identity of the test subject matches the known subject. The subject characterization data can be a probability density in a phase space in which at least two quasi-periodic variables based on the pulse wave (e.g., blood pressure and volume time-series data) are correlated.

13 Claims, 11 Drawing Sheets

*Operational Mode*

Operational Mode

| Variable → <br> Technique ↓ | Pressure Time Series | Pulse Wave Velocity | Volume Time Series | Blood Velocity | Electro-cardiogram |
|---|---|---|---|---|---|
| Tonometry | X | X | | | |
| Photo-plethysmography | | | X | | |
| Auscultation | X | | | | |
| Ultrasonic Velocimetry | | | X | X | |
| Laser Velocimetry | | | X | X | |
| Potentiometry | | | | | X |

*Fig. 6*

BIOMETRIC IDENTIFICATION SYSTEM USING PULSE WAVEFORM

BACKGROUND OF THE INVENTION

1. Field of the Invention

The present invention relates generally to the field of biometric identification systems. More specifically, the present invention discloses a system for biometric identification based on characteristics of the subject's pulse waveform.

2. Background of the Invention

Biometric identification is the process of recognizing or rejecting an unknown person as a particular member of a previously characterized set, based on biological measurements. The ideal biometric characterization is specific to the individual, difficult to counterfeit, robust to metabolic fluctuations, insensitive to external conditions, easily measured, and quickly processed.

Fingerprint, retinal, iris and facial scans are well-known biometric identification techniques relying on image processing. Images are two-dimensional, requiring sophisticated and computationally intensive algorithms, the analysis of which is often complicated by random orientation and variable scaling. Voice recognition is an example of biometric identification amenable to time-series analysis, an inherently simpler one-dimensional process.

Identity tracking/confirmation is the process of following the whereabouts of a known subject moving unpredictably among similar individuals, perhaps with deceptive intent. Tracking/confirmation is somewhat simpler than identification, because it merely requires distinguishing the subject from all others rather than distinguishing every individual from every other, and because continuous rather than episodic data are available. Biometric identity tracking/confirmation is the continuous verification that a body-mounted sensor has remained on the subject, and has not been surreptitiously transferred to an impostor. For the purposes of this application, the term "biometric identification" should be broadly construed to encompass both biometric identification in its narrower sense, as described above, and identity tracking/confirmation.

SUMMARY OF THE INVENTION

This invention provides a biometric identification system and method in which identity confirmation is based on the pulse wave of the subject. During an initial enrollment mode, pulse wave data for a known subject are used to generate subject characterization data for the known subject. During a subsequent operational mode, pulse wave data for a test subject are analyzed using the subject characterization data to confirm whether the identity of the test subject matches the known subject. The subject characterization data can be a probability density in a phase space in which at least two quasi-periodic variables based on the pulse wave (e.g., blood pressure and volume time-series data) are correlated.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 6 is a matrix illustrating the types of sensor techniques that can be employed to monitor a subject's pulse and generate different types of pulse-related data.

DETAILED DESCRIPTION OF THE INVENTION

Figure 1:
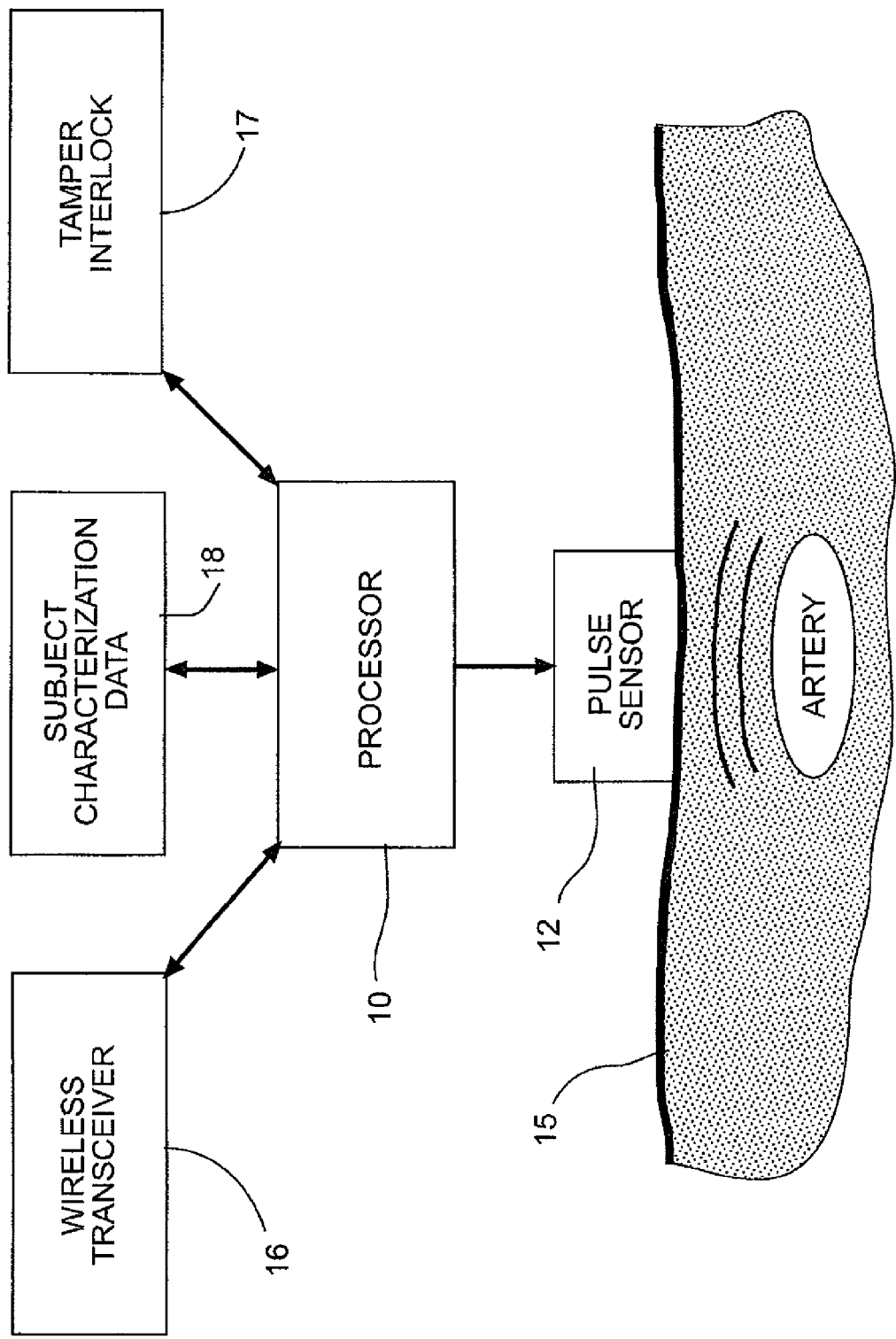
FIG. 1 is a system diagram for the present invention.

The present invention provides a biometric system for characterizing individuals by the non-invasive sensing of arterial pulse waves, for the purpose of identification and identity tracking/confirmation. FIG. 1 is a simplified system diagram for the present invention. The major components include a computer processor 10, and a pulse sensor 12 adjacent to the subject's tissue 15 that generates time-series data based on the subject's pulse waves.

As an overview, the processor 10 initially receives and analyzes this pulse wave data from the pulse sensor 12 for a known subject to generate subject characterization data 18 identifying the known subject. Thereafter, in normal operational mode, the processor 10 receives pulse wave data from the pulse sensor 12 for a test subject (who may or may not be the known subject). The processor 10 analyzes this pulse wave data in conjunction with the subject characterization data 18 to determine whether the test subject is the same as the known subject. For the purposes of this application, it should be understood that the phrase "test subject" refers to the person whose identity is being tested or confirmed during the operational mode of the present system.

Figure 2:
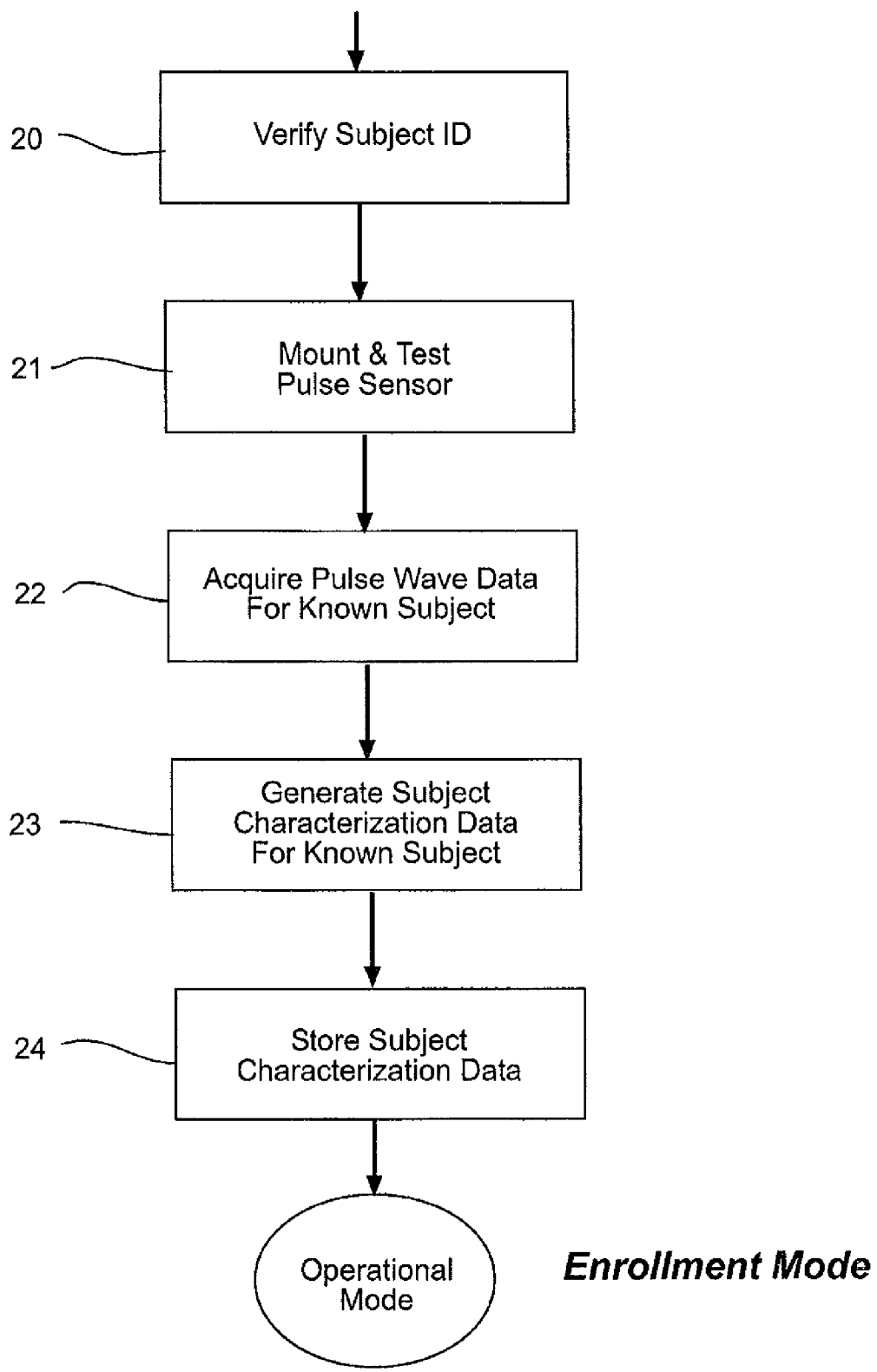
FIG. 2(a) is a flowchart of the enrollment mode of the present invention.
FIG. 2(b) is a flowchart of the operational mode of the present invention.
Figure 2:
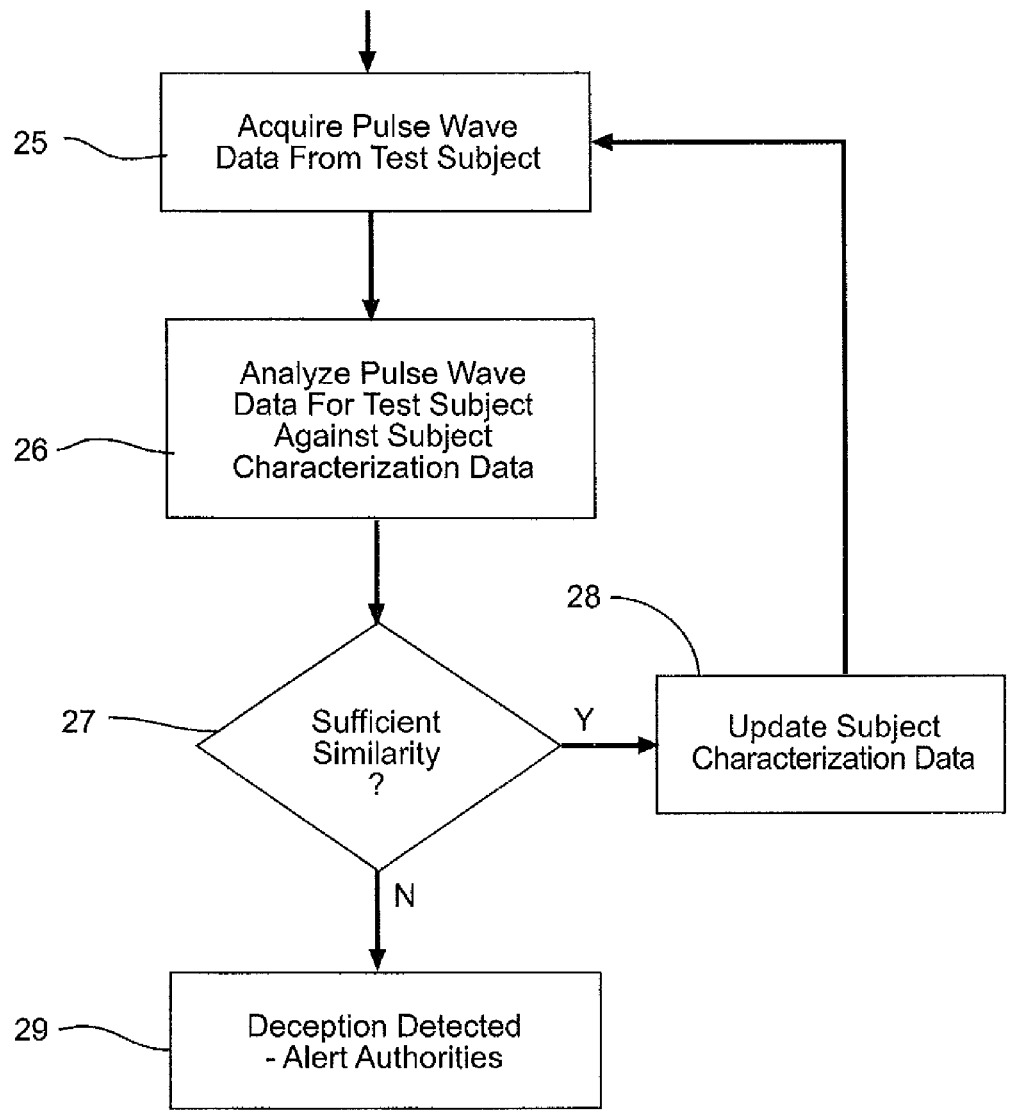

FIG. 2(a) is a flowchart of the enrollment mode employed to initially build subject characterization data 18 for a known subject. The operator first verifies the identity of the subject (step 20), and mounts and tests the pulse sensor 12 on the subject (step 21). The processor 10 acquires pulse wave data from the pulse sensor 12 for a brief period of time (step 22). The subject may be asked to undertake a range of activities to ensure the enrollment pulse wave data is representative of that which may be encountered over the subject's normal day-to-day activities. The processor 10 analyzes the enrollment pulse wave data and generates subject characterization data 18 for identifying the known subject (step 23). This subject characterization data 18 is stored for later use during the operational mode of the present system (step 24) as will be described below.

Following completion of the enrollment mode, the present system proceeds to operational mode during day-to-day monitoring of the subject. FIG. 2(b) is a flowchart of the operational mode. At selected time intervals or on a continuing basis, the processor 10 acquires pulse wave data from the pulse sensor 12 for the test subject (step 25). The processor 10 analyzes this pulse wave data using the subject characterization data 18 (step 26). Based on this analysis, the processor determines whether there is a sufficient degree of similarity between the pulse wave characteristics of the known subject (from the subject characterization data 18) and the test subject to conclude that these subjects are the same person (step 27). If so, the processor 10 may update the subject characterization data 18 to include the current pulse wave data (step 28) and then loop back to step 25. Otherwise, if the processor 10 determines that the current test subject is not the same as the known subject, an alarm can be activated to signal that deception has been detected (step 29). The processor can also remotely alert the authorities via a wireless transceiver 16.

FIGS. 5(a)-5(f) show examples of six distinct pulse waves. Qualitative characteristics useful for identification include the abruptness of systolic onset (leading edge), the roundedness of systole (peak), the concavity of diastolic onset (trailing edge), the presence or absence of the dichrotic notch (dip) and other oscillations, and the timing of oscillatory features relative to systole. In contrast to the three most common hemodynamic measurements systolic pressure, diastolic pressure, and pulse rate—these characteristics are persistent through cycles of sleep and waking, leisure and exertion, and relaxation and stress. Pulse wave characteristics do evolve as the subject ages, but these changes are negligible over the identity-tracking/confirmation time scale.

Figures 5A, 5B, 5C, 5D, 5E, 5F:
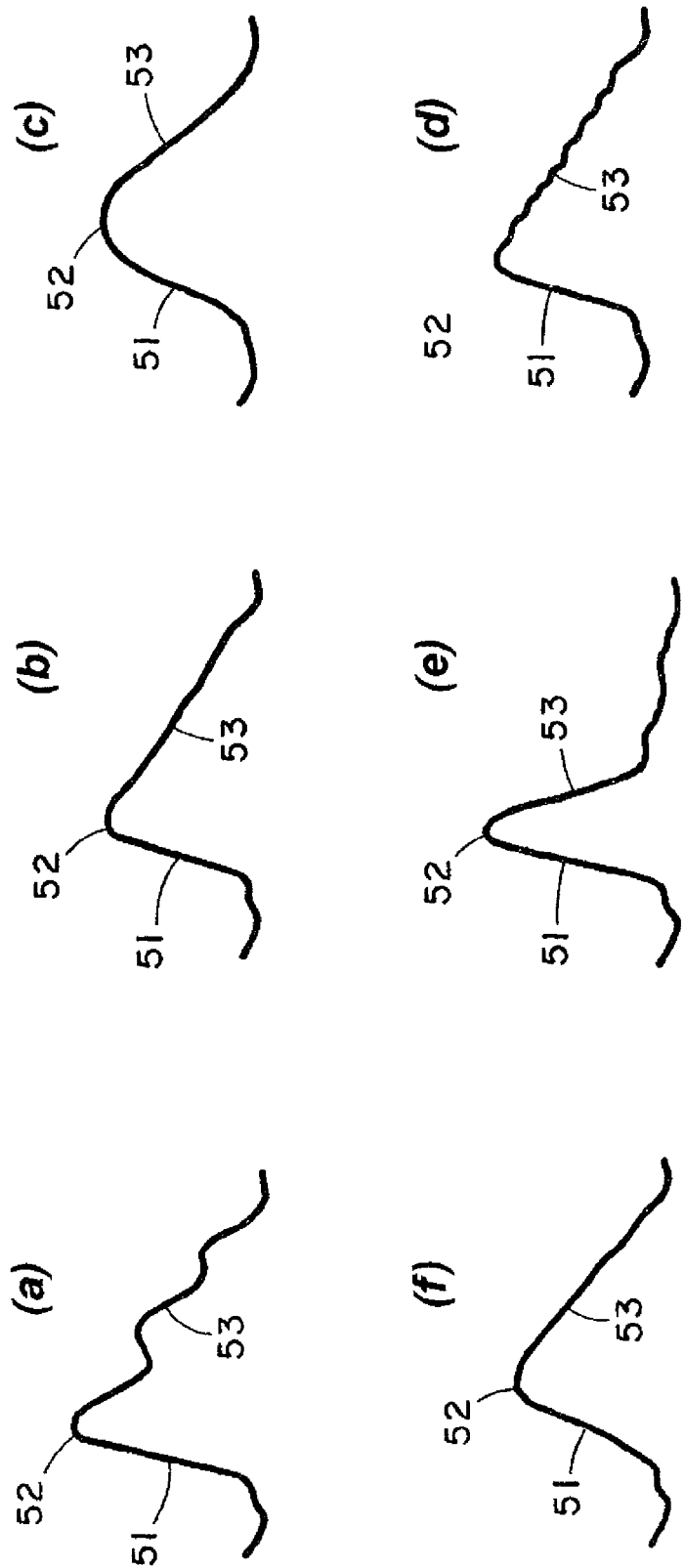
FIGS. 5(a)-5(f) show examples of six distinct pulse waves illustrating the potential of pulse wave identification and identity tracking/confirmation.

The leading edge 51 of the pulse wave in FIG. 5(a) has a fast slope. The peak 52 of the pulse wave has a rounded, but narrow crest that is not delayed. The trailing edge 53 of the pulse wave exhibits dicrotism. In contrast, the trailing edge 53 of the pulse wave in FIG. 5(b) has no dicrotism. The peak 52 of the pulse wave in FIG. 5(c) is delayed and has a round crest. The pulse wave in FIG. 5(f) has a leading edge 51 with a slower slope, a peak 52 that is delayed but not rounded, and a trailing edge 53 with no dicrotism. FIG. 5(e) shows a pulse wave with a trailing edge 53 that exhibits deep dicrotism. FIG. 5(d) shows a pulse wave with a trailing edge 53 having a series of small waves.

FIG. 6 is a matrix illustrating the types of measurement techniques that can be employed to monitor a subject's pulse and generate different types of pulse-related data. Possible arterial blood transport measurements include the blood pressure time-series, the pulse wave velocity, the blood volume time-series, and blood velocity. The electrocardiogram (EKG), although not a transport measurement per se, should also be considered due to its own potential for identification, and as a master timer for synchronous detection.

Pressure and volume time-series are local measurements in the sense of requiring but a single bodily contact, but are global in the sense that the heart and remote features of the arterial system influence the measurement through forcing, viscous drag, and pressure wave reflections. Thus the entire subject may be characterized using a point sensor, as with established biometric identification techniques such as fingerprint and retinal scans.

Identification and tracking/confirmation should be non-invasive (i.e., the pulse sensor 12 should contact but not penetrate the subject). All of the variables listed above can be measured non-invasively by the pulse sensor 12, using techniques such as tonometry, photoplethysmography, auscultation, ultrasonic Doppler flowmetry, laser Doppler flowmetry and potentiometry.

Figure 3:
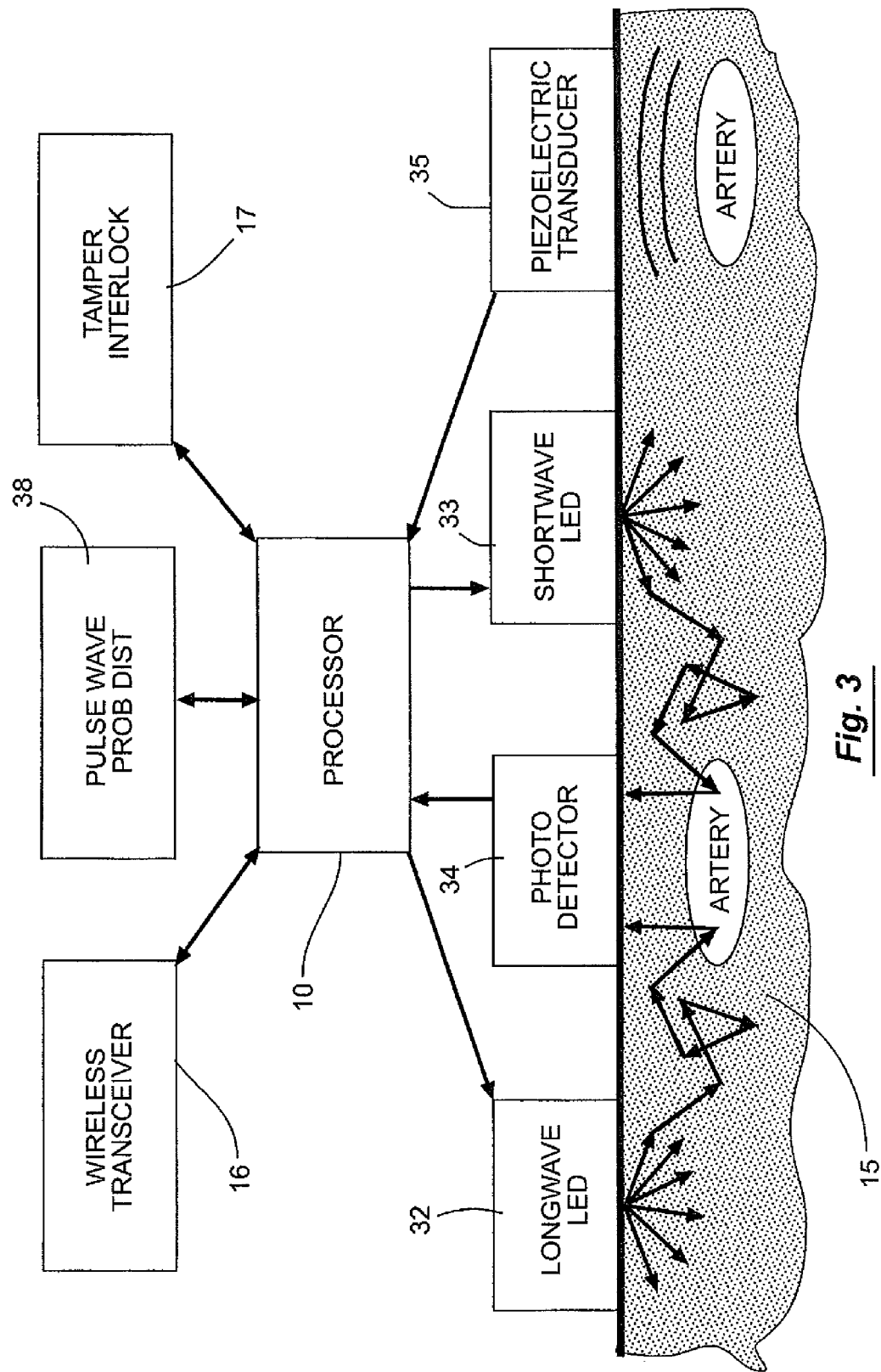
FIG. 3 is a system diagram of an embodiment of the present invention using blood pressure and pulsatile blood volume as the pulse wave data.

Tonometry and photoplethysmography appear to be the two most promising pulse-wave sensing techniques for subject identification, and will serve to illustrate the invention. A piezoelectric transducer can perform tonometry, as shown in FIG. 3, and is core to the compact commercial instrument "PulsePen" marketed by DiaTecne s.r.l. of Milan, Italy. Two light-emitting diodes 32, 33 and a photodetector 34 can perform photoplethysmography as shown in FIG. 3, the dominant technology in the pulse-oximeter market.

Simultaneous tonometry and photoplethysmography may be particularly effective. The relative magnitude of the pressure and volume swings is a measure of arterial elasticity, and the phase lag from the pressure to the volume peak gives a hemodynamic parameter called the Womersley number.

Pressure and volume time-series are attractive hemodynamic variables, since each provides non-local information from a single-contact sensor. These may be implemented by tonometry and photoplethysmography, respectively. Both technologies are simple, low-power, and mature bases of commercial sensors.

Thus, the present invention can be based on any of the more promising hemodynamic variables, sensing techniques, and signal processing algorithms. This example is illustrative only, and should not be construed as our relinquishment of the alternative variables, techniques, and algorithms discussed here, or uncovered later, for the purposes of pulse wave identification and identity tracking/confirmation. In particular, a wide variety of signal processing techniques in either the time domain or frequency domain can be applied to the pulse wave data output by the pulse sensor 12 to generate subject characterization data 18.

Subject characterization can be approached in any of several ways: (1) A classification according to qualitative features of the pulse wave, such as the relative timing of the systolic peak and the inflection point; (2) A local scalar parameter, such as the arterial elasticity or Womersley number; (3) A non-local scalar parameter, such as the time delay between forward and reflected pressure waves, which is equal to the distance to the reflecting structure divided by the pulse wave velocity; (4) A vector parameter, such as that resulting from fitting a Windkessel RCL-network model (see, for example, "Arterial pressure contour analysis for estimating human vascular properties", T. B. Watt et. al., Journal of Applied Physiology 40, pp. 171-176 (1976)); or (5) A learned probability density in phase space, such as the delayed correlation of either the pressure or the volume with itself, or the simultaneous correlation of pressure and volume. The qualitative approach has a parallel in fingerprint analysis, in which the Henry system of classification uses loops, whorls, and arches to sort fingerprints. While qualitative classification undoubtedly helpful in forensics and cardiology, it has shortcomings that may limit its appropriateness for this invention.

To suffice in itself, a scalar parameter needs a spread among individuals of a population that is large compared to the variation of a particular individual from one occasion to another. That any single pulse wave parameter fits the bill is dubious: The population spread of pulse wave parameters is not dissimilar to that of adult height, and while height is useful in identification, few would assert that height alone is sufficient.

A vector parameter may be better suited for subject identification, owing to its multiple dimensionality. A Windkessel fit has demonstrated pairs of individuals distinguishable from each other by their arterial compliance (C), but not by their viscous resistance (R), and vice versa ("Identification of vascular parameters based on the same pressure pulses [sic] waves used to measure pulse wave velocity", A. S. Ferreira et. al., 23rd Annual International Conference of the IEEE Engineering in Medicine and Biology Society (2001)). However, the circulatory system is not a passive electrical circuit, being both non-linear and non-local; and poorly fitting models tend to yield unstable parameter values.

The learned-probability approach recommends itself in several ways: (1) It can't bomb out because of an individual's lack of a common but non-universal hemodynamic feature, such as the dichrotic notch; (2) It utilizes all data, rather than heavily weighting prominent features, such as the systolic peak; (3) It relies on no artificial or simplistic assumptions about the dynamics, as does the Windkessel approach; and (4) It naturally yields the optimal decision and probability of error in detecting identity deception. Therefore, the learned-probability approach will serve to illustrate the invention.

In the present context, "phase space" is a multi-dimensional (D-dimensional) space in which a quasi-periodic variable is correlated with (D−1) other measurements. The other measurements can be the same variable measured at various times in the past, or other contemporary variables, or a combination. The D measurements form a vector that traces an "orbit" in phase space. A strictly periodic phenomenon will follow the same orbit over and over, and will soon be utterly predictable. A phenomenon that varies from cycle to cycle will yield a blurred, probabilistic orbit.

Figure 7:
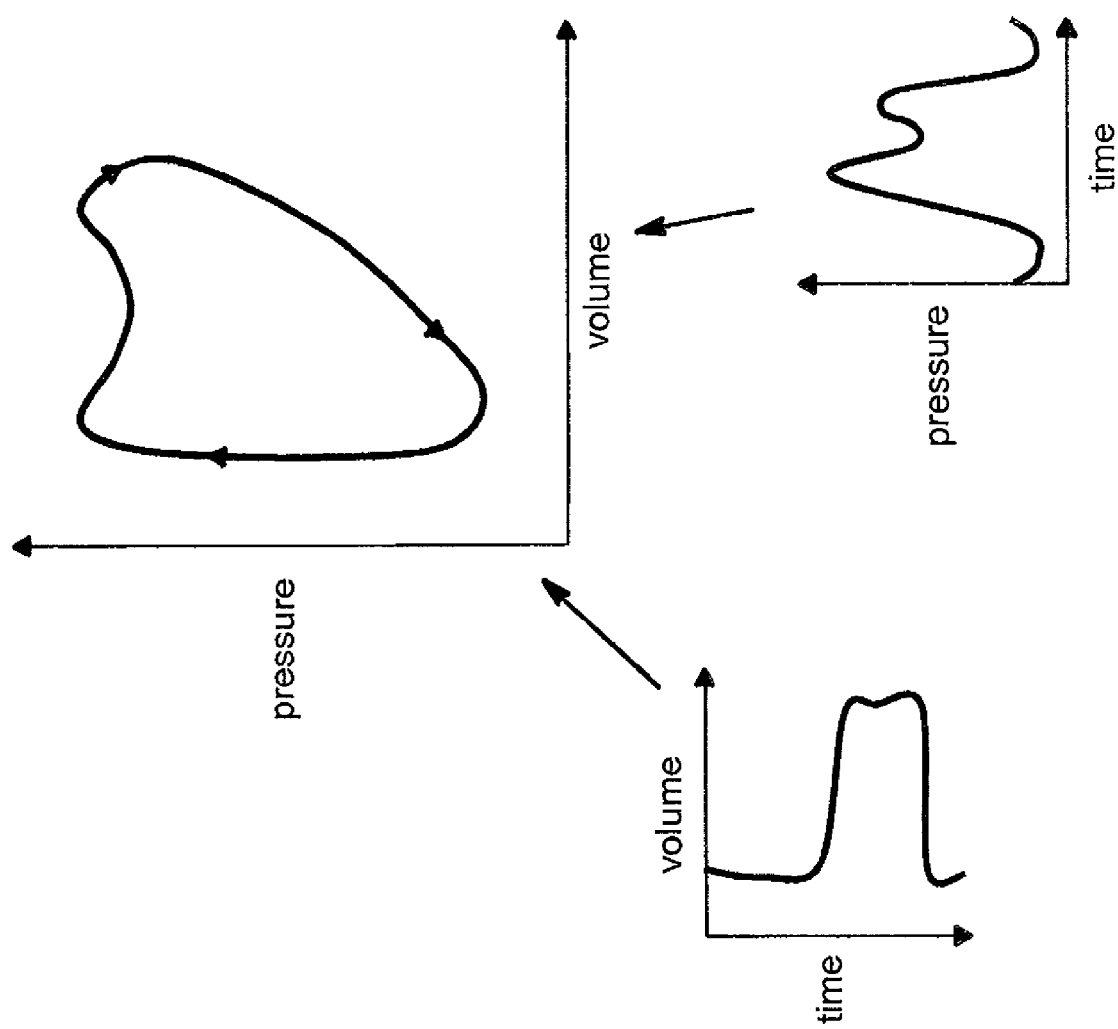
FIG. 7 is a graph showing the representation of two time-series (i.e., blood pressure and volume) in a two-dimensional phase space.
Figure 8:
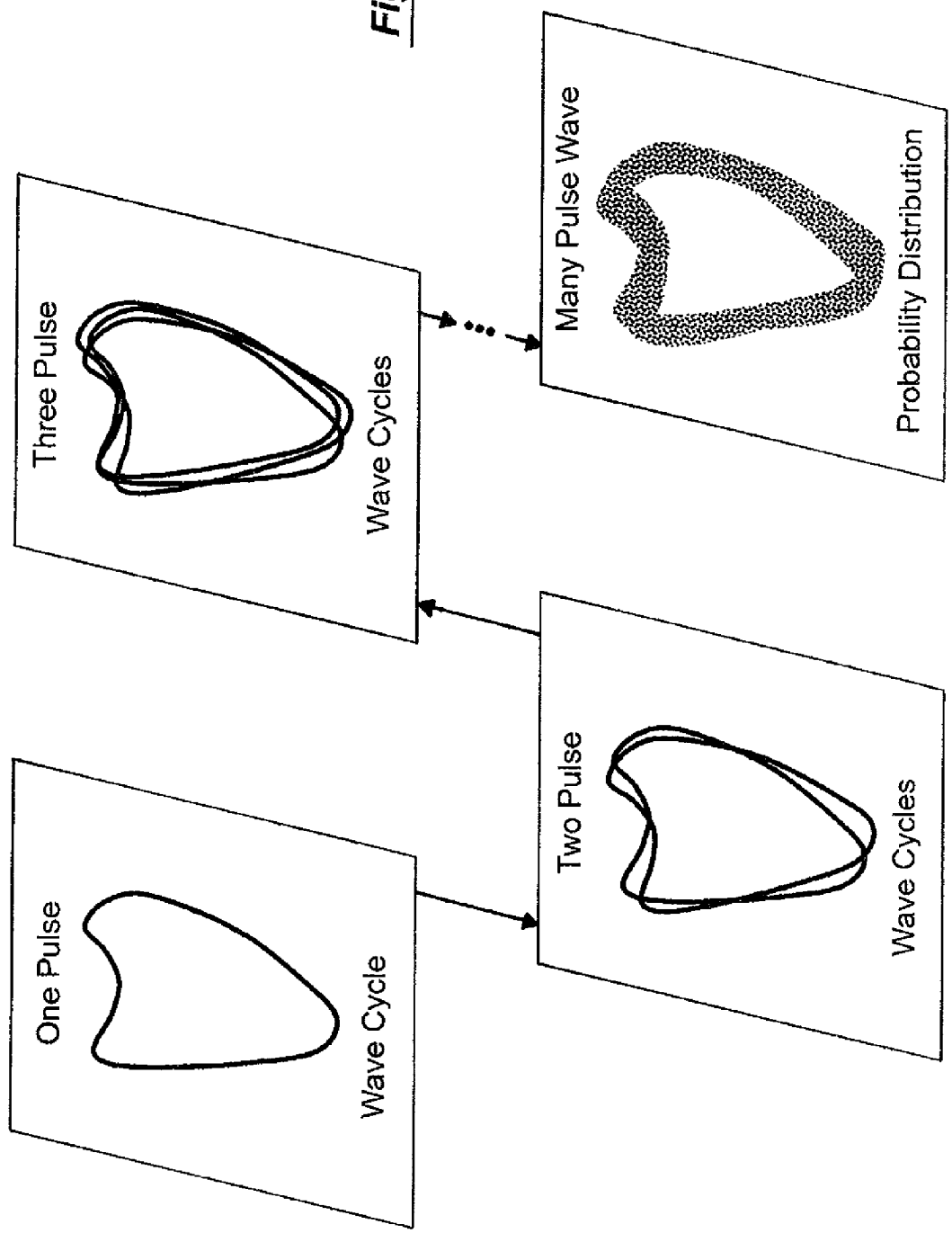
FIG. 8 is a diagram illustrating how a pulse wave probability distribution can be built up from pulse wave data over many wave cycles.

It happens that blood volume lags blood pressure by a fraction of a cycle, so a reasonable choice is the 2-D phase space comprising the present values of pressure and volume. FIG. 7 depicts the reduction of pressure and volume time-series into a pressure versus volume orbit in phase space. FIG. 8 is a diagram illustrating how a pulse wave probability distribution can be built up from pulse wave data over many wave cycles.

The phase space domain is usually just the outer product of its scalar variable domains. With 8-bit analog-to-digital conversion (ADC), a 2-D phase space needs but a modest 65,536-address memory. An 8-bit ADC is probably adequate, considering the small dynamic range and noisiness of the signals. An example pressure (volume) domain is 64 mmHg to 192 mmHg, in 0.5 mmHg steps (1/2 to 3/2 the average volume, in steps of 1/256).

The phase space range should be appropriate for storing a probability—for instance, an unsigned integer. Since the orbit visits some phase space cells much more frequently than others, the integer must have sufficient dynamic range, say 16 bits. Thus, the example phase space probability density memory requirement is 128 kilobytes. In other words, the phase space is effectively a 2-D array of cells or elements, each of which store an integer value representing the probability associated with a particular pair of a blood pressure and volume values for the subject. This phase space can be referred to as a pulse wave probability distribution (or PWPD)

FIG. 3 is a system diagram of an embodiment of the present invention using blood pressure and pulsatile blood volume as the pulse wave data used for generating a pulse wave probability density 38 for the purpose of subject characterization. The embodiment illustrated in FIG. 3 also employs a photoplethysmograph as the pulse wave sensor. Two light-emitting diodes 32, 33 irradiate the subcutaneous tissue 15, and a common photodetector 34 senses the backscattered light. One LED 32 emits at a longer wavelength whose absorption is dominated by oxygenated hemoglobin, and the other LED 33 emits at a shorter wavelength whose absorption is dominated by deoxygenated hemoglobin. The LEDs 32, 33 can be modulated out of phase to temporally multiplex their signals, and the pulsatile blood volume is proportional to the difference signal.

Figure 4:
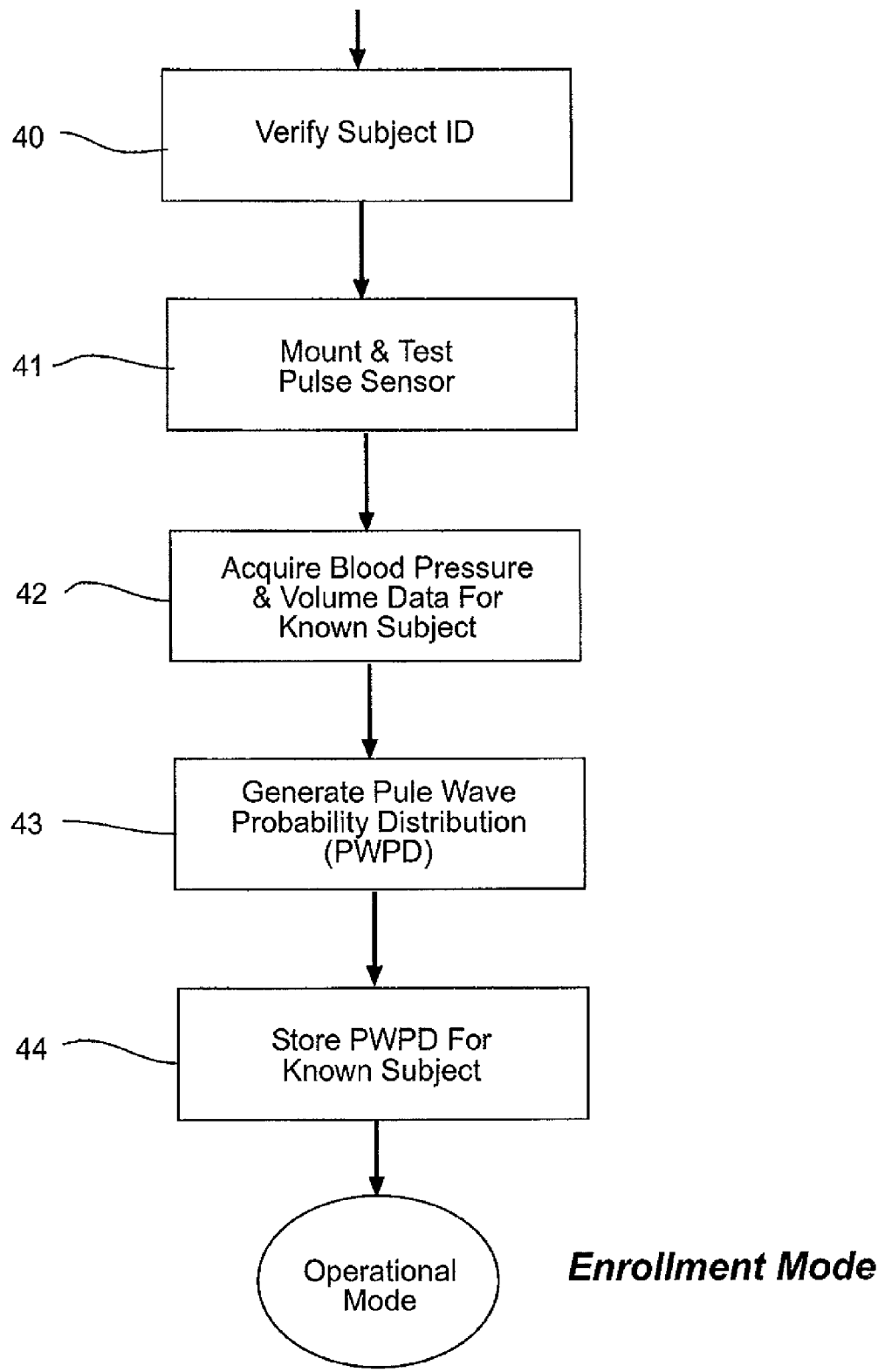
FIG. 4(a) is a flowchart for the enrollment mode for the embodiment of the present invention in FIG. 3.
FIG. 4(b) is a flowchart of the operational mode for the embodiment of the present invention in FIG. 3.
Figure 4:
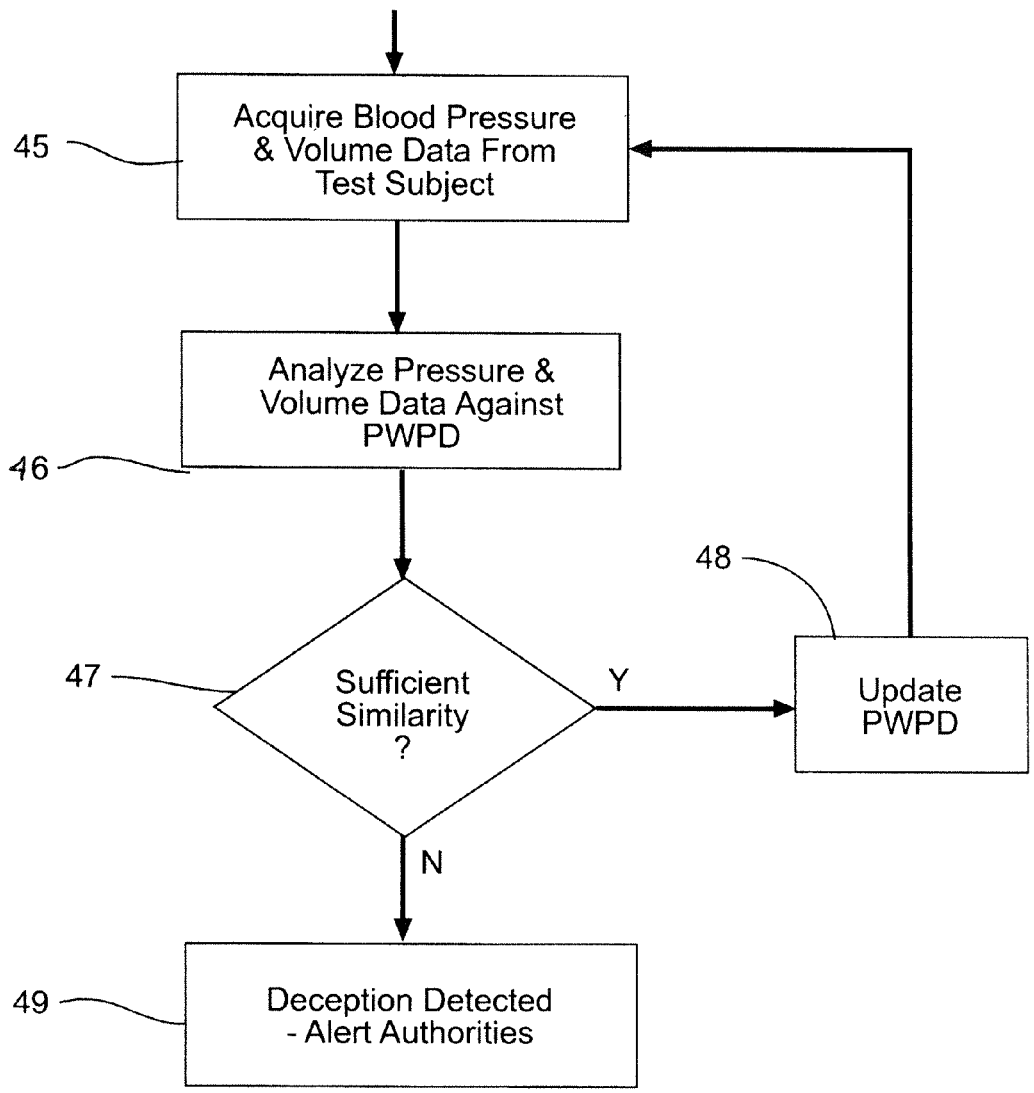

A known subject's pulse wave probability density 38 is initially acquired during the brief enrollment period, consisting of the subject wearing the pulse sensor 12 while engaging in various activities. FIG. 4(a) is a flowchart for this enrollment mode for the embodiment of the present invention illustrated in FIG. 3. Here again, the operator verifies the identity of the subject (step 40), and mounts and tests the LEDs 32, 33 and photodetector 34 on the subject (step 41). The processor 10 acquires blood pressure and volume data from the photodetector 34 for a brief period of time (step 42). The processor analyzes this data to generate a pulse wave probability distribution (PWPD) 38 for the known subject in step 43. In particular, the pulse wave probability density 38 can be generated from blood pressure time-series data correlated with blood volume time-series data. The PWPD 38 is then stored for later use in the operational mode (step 44).

After enrollment, the present monitoring system moves to operational mode. FIG. 4(b) is a flowchart of the operational mode for the embodiment of the present invention shown in FIG. 3. During each iteration, the processor 10 acquires blood pressure and volume data from the photodetector 34 for the test subject (step 45). The processor 10 analyzes this blood pressure and volume data to determine there is sufficient similarity between the pulse wave characteristics of the known subject and the test subject currently wearing the present unit (steps 46 and 47).

More specifically, the pulse wave probability distribution 38 serves as a look-up table for the probability associated with pairs of blood pressure and volume values measured during operational mode. In particular, the processor 10 retrieves from the pulse wave probability distribution 38 the probability associated with the current blood pressure and volume values. While not perfectly predictive, the pulse wave probability density 38 contains a great deal of information about the relationship of different phases of the cycle to each other, and can be quite specific to a subject, without assuming any particular model.

In the preferred embodiment of the present invention, deception is detected when the compound probability of measuring the latest N data is deemed sufficiently small. More specifically, a deception is judged when the cost of erroneously regarding the subject as truthful exceeds the cost of erroneously regarding the subject as deceptive: $C(t|D) \times P(D|M) > C(d|T) \times P(T|M)$, where $C(t|D)$ is the penalty for judging the subject truthful when in fact deceptive, and $P(D|M)$ is the (unknown) conditional probability of deception given the measurement M, and vice versa for the right-hand side of the inequality.

Bayes' theorem states $P(D|M) \times P(M) = P(D,M) = P(M|D) \times P(D)$, where $P(M)$ is the (inconsequential) a priori probability of measuring M, $P(D,M)$ is the (undesired) joint probability of deception and measuring M, $P(M|D)$ is the (known) conditional probability of measuring M given deception, and $P(D)$ is the (estimated) probability of deception. Substituting into the cost condition and rearranging gives $P(M|D)/P(M|T) \times P(D)/P(T) > C(d|T)/C(t|D)$. These factors are all known or estimated: $P(M|D)$ is given by the average of all subjects' probability densities, assuming this average represents the general population, and the subject is as likely to pass off the sensor to anyone as to anyone else; $P(M|T)$ is given by the subject's own probability density; $P(D)$ is estimated from a subject's past behavior (e.g. a subject who has not attempted deception in a year has at most a $10^{-6}$ probability of attempting deception in any 30-second measurement period); $P(T)$ is merely $1-P(D)$; and $C(d|T)$ and $C(t|D)$ are input parameters.

Figure 9:
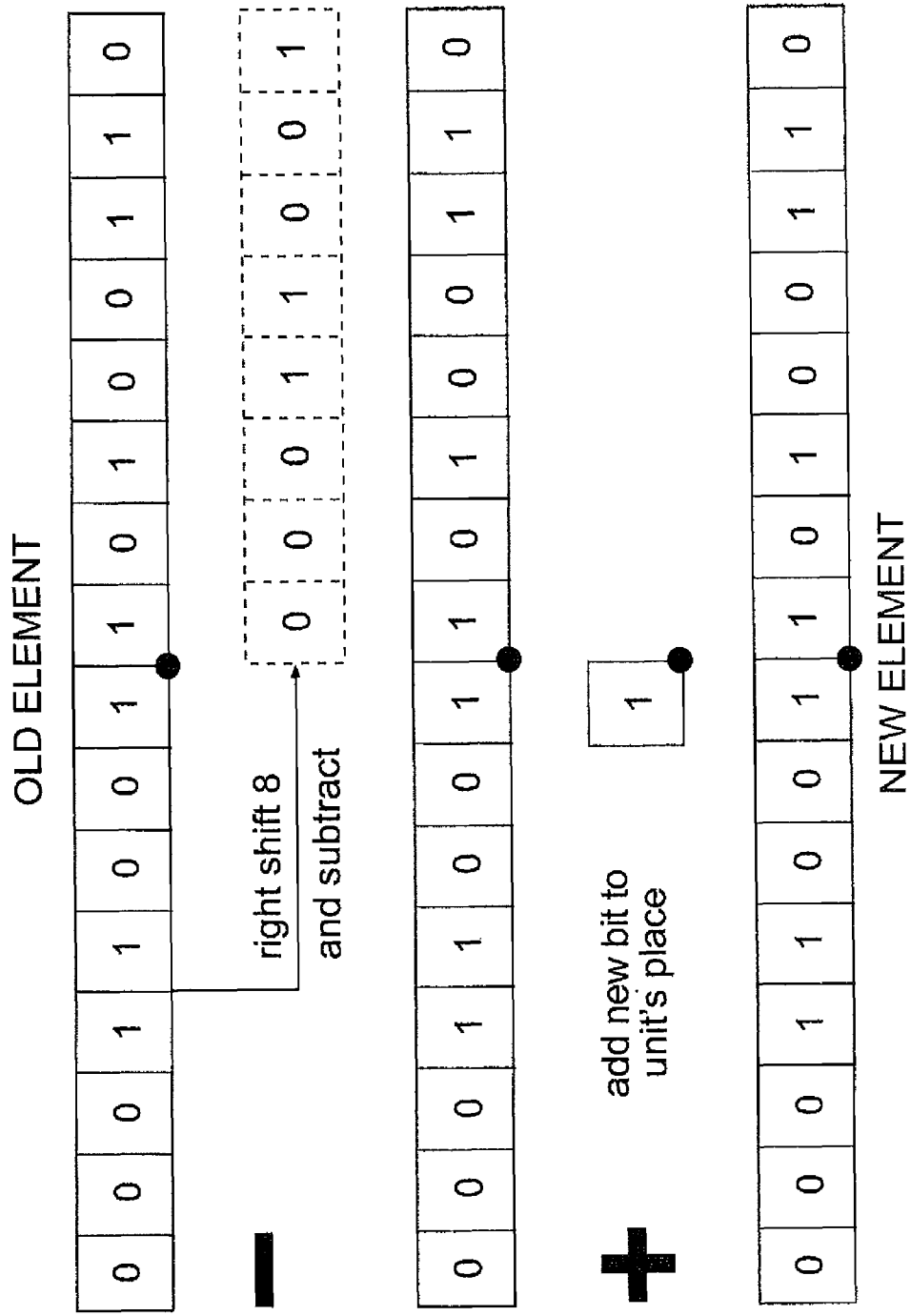
FIG. 9 is a diagram showing an efficient algorithm using integer operations for updating a pulse wave probability distribution 38.

If the processor 10 determines deception has occurred, an alarm can be activated and the authorities are alerted (step 49). Otherwise, before returning to step 45 to begin the next iteration, the blood pressure and volume data from this iteration are employed to update the pulse wave probability density 38 (step 48). In order to weight new data more than old data, and to prevent overflow, the accumulated probability density is continuously devalued. For example, the pulse wave probability density 38 can be efficiently updated in step 48 of FIG. 4(b) using the elementary operations illustrated in FIG. 9. After each measurement, and for each element in the phase space, devalue the existing probability density (e.g., by multiplying by 255/256) to account for the decay of information's relevance over time, then add a new data bit (e.g., 1) to the unit's place. The actual probability can be normalized to the sum of elements over the space, of course, but this conventional normalization is not needed in the following algorithm, saving computations.

The present invention can be employed in a number of possible fields of use. For example, it can be used as a self-contained, mobile unit for identity confirmation as part of an alcohol monitoring system, such as an alcohol monitoring bracelet or a vehicle interlock system to prevent operation by an unauthorized or alcohol-impaired driver. The present invention can also be used to remotely track and verify the identity of persons at a secure facility or under house arrest. For example, this identity verification can be performed continually, at selected time intervals, or at selected locations in the facility.

Presently, many automated identity confirmation systems in secure facilities read a magnetic stripe or barcode on badges, or rely on biometrics such as fingerprint or retinal scans. The drawbacks to existing approaches include: (1) Badge-based identity confirmation is easily subverted, providing security too weak for many applications; (2) Biometric approaches can be intrusive (e.g., retinal scanning) or prone to fouling via repeated contact (e.g., fingerprint scanning); (3) Biometric approaches based on optical imaging are expensive, limiting their use to identity checkpoints and major equipment; (4) Identity checkpoints require hardware installed at fixed locations, typically the gates of the facility and the thresholds between areas of differing security levels, so that reconfiguring the security zone layout entails significant renovation; and (5) Identity checkpoints provide only occasional identity confirmation (when the subject attempts passage), rather than continual identity confirmation.

The secure-facility embodiment of the present invention can be implemented using a sensor attached on the subject upon entering the facility (e.g., as a bracelet), worn throughout the duration on the premises as ensured by tamper-proof features, and removed upon exiting the facility. The sensor continually confirms the identity and reports the whereabouts of the subject via a wireless link 16. The sensor can also include a direct port for enabling equipment authorized for use by the subject. Alternatively, the sensor could be implemented as a fixed (e.g., wall-mounted) unit at selected doors and gates within the facility.

In one embodiment of the present invention, a piezoelectric transducer 35 (e.g., a piezoelectric film) produces an analog signal proportional to the pulse. This can be in place of, or in addition to the optical pulse sensors discussed above. The secure bracelet is placed on the subject and pulse wave characteristics are immediately acquired and stored in a lookup table for future comparison/verification. A analog-to-digital converter transforms the pulse wave to a digital time series. The processor 10 compares the time series to the pulse wave probability distribution stored in local memory.

If the time-series data matches the probability distribution, the processor 10 confirms the subject's identity, and updates the stored probability distribution with new data. If the time series does not match, the processor 10 deems the identity of the test subject to be unconfirmed, and does not update the probability distribution. Either way, the processor 10 can report its decision regarding the test subject's identity to a remote central security manager via a radio-frequency (RF) communications link 16. The processor 10 can also report the test subject's identity to an external device attached to a direct port associated with the present system.

The present invention can also include a location sensor (e.g., a GPS unit) in communication with the processor 10. This enables the processor 10 determine the physical location of the subject. For example, the processor 10 can log the subject's path within secure facility, or then trigger an alarm or report to authorities if the subject moves into an unauthorized area. In mobile applications, such as a bracelet or vehicle interlock system, the processor 10 can monitor and communicate the subject's location to authorities via the wireless link 16.

A tamper interlock system 17 detects attempts to remove the sensor, or otherwise prevent its working properly. The tamper system 17 is enabled when a security officer fits the sensor to the subject upon entering the premises, and can only be disarmed by the security officer when the sensor is removed and the subject leaves.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. A method for biometric identity confirmation of a subject having a pulse, said method comprising:
   initially acquiring and analyzing pulse waveform data for a known subject to generate subject characterization data identifying the known subject, wherein the subject characterization data is a probability density in a phase space in which a first quasi-periodic variable based on the pulse waveform is correlated with at least a second quasi-periodic variable based on the pulse waveform; and
   during a subsequent operational mode, acquiring and analyzing pulse waveform data for a test subject to confirm whether the identity of the test subject matches the known subject based on the probability values associated with the pulse waveform data for the test subject.

2. The method of claim 1 wherein the pulse waveform data comprises blood volume time-series data.

3. The method of claim 1 wherein the pulse waveform data comprises blood velocity time-series data.

4. The method of claim 1 wherein the pulse waveform data comprises the pulse wave velocity.

5. The method of claim 1 wherein the pulse waveform data comprises electro-cardiogram data.

6. The method of claim 1 wherein confirmation of the identity of the test subject is used to control a vehicle interlock system.

7. The method of claim 1 wherein the probability density is initially generated from pulse waveform data acquired during an enrollment mode and then updated with pulse waveform data acquired during the operational mode.

8. The method of claim 1 wherein the pulse waveform data comprises blood pressure time-series data.

9. The method of claim 1 wherein the probability density is generated from blood pressure time-series data correlated with blood volume time-series data.

10. The method of claim 1 wherein the probability density is initially generated from pulse waveform data acquired during an enrollment mode and then updated with pulse waveform data acquired during the operational mode.

11. An apparatus for biometric confirmation of the identity of a test subject in an alcohol monitoring system, said test subject having a pulse, said apparatus comprising:
- a light source directing light into the subcutaneous tissue of a subject;
- a photo-detector sensing the backscattered light from the tissue of a subject; and
- a processor in communication with the photo-detector to generate pulse waveform data for the subject based on light absorption by the tissue, said processor having:
  - (a) an initial enrollment mode, in which pulse waveform data are analyzed for a known subject to generate subject characterization data identifying the known subject, wherein the subject characterization data is a probability density in a phase space in which a first quasi-periodic variable based on the pulse waveform is correlated with at least a second quasi-periodic variable based on the pulse waveform; and
  - (b) a subsequent operational mode, in which pulse waveform data are analyzed for a test subject in an alcohol monitoring system using the subject characterization data for the known subject to confirm whether the identity of the test subject matches the known subject based on the probability values associated with the pulse waveform data for the test subject.

12. The apparatus of claim 11 wherein the light source produces light having a first wavelength whose absorption by tissue is dominated by oxygenated hemoglobin and a second wavelength whose absorption by tissue is dominated by deoxygenated hemoglobin, and wherein the processor generates pulse waveform data indicating blood pressure and blood volume in the tissue based on light absorption at the first and second wavelengths.

13. The apparatus of claim 12 wherein the subject characterization data comprise a probability density in a phase space in which blood pressure time-series data are correlated with blood volume time-series data.

\* \* \* \* \*